United States Patent [19]

Zelson

[11] Patent Number: 5,025,800
[45] Date of Patent: Jun. 25, 1991

[54] CONTRACEPTIVE DEVICE

[76] Inventor: Steve T. Zelson, 209 Mulberry La., Larchmont, N.Y. 10538

[21] Appl. No.: 148,568

[22] Filed: Jan. 26, 1988

[51] Int. Cl.$^5$ ............................ A61F 6/04; A61F 6/06
[52] U.S. Cl. ..................................... 128/844; 128/832
[58] Field of Search ............... 128/844, 842, 830, 832; 604/349

[56] References Cited

U.S. PATENT DOCUMENTS

| | | | |
|---|---|---|---|
| 2,326,159 | 8/1943 | Mendel | 604/349 |
| 2,410,460 | 11/1946 | Robinson | 604/349 |
| 2,577,345 | 12/1951 | McEwen | 128/844 |
| 2,586,674 | 2/1952 | Lonne | 604/349 |
| 3,496,938 | 2/1970 | Furuse | 128/844 |
| 4,349,026 | 9/1982 | Miyata | 604/349 |
| 4,415,548 | 11/1983 | Reddy | 128/844 |
| 4,446,860 | 5/1984 | Gutnik | 128/844 |
| 4,722,888 | 2/1988 | Broder et al. | 530/387 |
| 4,771,482 | 9/1988 | Shlenker | 2/161 R |
| 4,783,446 | 11/1988 | Neushul | 514/934 |
| 4,784,942 | 11/1988 | Harley | 435/7 |
| 4,788,181 | 11/1988 | Driscoll et al. | 536/29 |
| 4,790,835 | 12/1988 | Elias | 604/349 |
| 4,795,425 | 1/1989 | Pugh | 604/349 |
| 4,795,739 | 1/1989 | Lifson et al. | 514/8 |
| 4,818,538 | 4/1989 | Rideout et al. | 514/962 |
| 4,898,184 | 2/1990 | Skurkovich | 128/844 |

FOREIGN PATENT DOCUMENTS

| | | | |
|---|---|---|---|
| 0267218 | 11/1913 | Fed. Rep. of Germany | 604/349 |
| 0641521 | 8/1928 | France | 604/349 |
| 0326719 | 3/1930 | United Kingdom | 604/349 |

*Primary Examiner*—C. Fred Rosenbaum
*Assistant Examiner*—Sharon Rose
*Attorney, Agent, or Firm*—Steve T. Zelson

[57] ABSTRACT

This invention relates to contraceptive devices. More particularly, this invention relates to novel contraceptive devices for males and females which provide immunological barriers to the spread of sexually transmitted diseases along with related methods to prevent the spread of these diseases.

28 Claims, 8 Drawing Sheets

```
CAACCCCAGACCCCATTTCTGTCCCCTCCTACTCTCAGCCTCCTCCTCCTCCTCGGCCAGCCCACA ATG AAC CGG
                                                                   met asn arg
                                                                           -1 gly val pro phe arg his leu leu val leu gln leu leu ala leu pro ala ala thr
GGA GTC CCT TTT AGG CAC TTG CTT GTG CTG CAA CTG CTG GCG CTC CCA GCA GCC ACT
-20                          -10 gln gly asn lys val val leu gly lys lys gly asp thr val glu leu thr cys thr
CAG GGA AAC AAA GTG GTG CTG GGC AAA AAA GGG GAT ACA GTG GAA CTG ACC TGT ACA
+1                   +10                                              * ala ser gln lys lys ser ile gln phe his trp lys asn ser asn gln ile lys ile leu
GCT TCC CAG AAG AAG AGC ATA CAA TTC CAC TGG AAA AAC TCC AAC CAG ATA AAG ATT CTG
+20                          +30 gly asn gln gly ser phe leu thr lys gly pro ser lys leu asn asp arg ala asp ser
GGA AAT CAG GGC TCC TTC TTA ACT AAG GGT CCA AGC CTG AAT GAT CGC GCT GAC TCA
+40                                  +50
```

FIG.6(cont'd-a)

```
+60
    arg arg ser leu trp asp gln gly asn phe pro leu ile ile lys asn leu lys ile glu
    AGA AGA AGC CTT TGG GAC CAA GGA AAC TTC CCC CTG ATC ATC AAG AAT CTT AAG ATA GAA
+80                                   *
    asp ser asp thr tyr ile cys glu val glu asp gln lys glu glu val gln leu leu val
    GAC TCA GAT ACT TAC ATC TGT GAA GTG GAG GAC CAG AAG GAG GAG GTG CAA TTG CTA GTG
+100
    phe gly leu thr ala asn ser asp thr his leu leu gln gly gln ser leu thr leu thr
    TTC GGA TTG ACT GCC AAC TCT GAC ACC CAC CTG CTT CAG GGG CAG AGC CTG ACC CTG ACC
+120                                                    *
    leu glu ser pro pro gly ser ser pro ser val gln cys arg ser pro arg gly lys asn
    TTG GAG AGC CCC CCT GGT AGC AGT CCC TCA GTG CAA TGT AGG AGT CCA AGG GGT AAA AAC
+140
    ile gln gly gly lys thr leu ser val ser gln leu glu leu gln asp ser gly thr trp
    ATA CAG GGG GGG AAG ACC CTC TCC GTG TCT CAG CTG GAG CTC CAG GAT AGT GGC ACC TGG
+160    *
    thr cys thr val leu asn gln lys lys lys val glu phe lys ile asp ile val val leu
    ACA TGC ACT GTC TTG AAC CAG AAG AAG AAG GTG GAG TTC AAA ATA GAC ATC GTG GTG CTA
```

FIG.6(cont'd-b)

```
+180
ala phe gln lys ala ser ser ile val tyr lys lys glu gly glu gln val glu phe ser
GCT TTC CAG AAG GCC TCC AGC ATA GTC TAT AAG AAA GAG GGG GAA CAG GTG GAG TTC TCC +200
phe pro leu ala phe thr val glu lys leu thr gly ser gly ser gly glu leu trp trp gln ala
TTC CCA CTC GCC TTT ACA GTT GAA AAG CTG ACG GGC AGT GGC AGT GGC GAG CTG TGG TGG CAG GCG +220
glu arg ala ser ser ser lys ser ser trp ile thr phe asp leu lys asn lys glu val ser
GAG AGG GCT TCC TCC TCC AAG TCT TGG ATC ACC TTT GAC CTG AAG AAC AAG GAA GTG TCT +240
val lys arg val thr gln asp pro lys leu gln met gly lys lys leu pro leu his leu
GTA AAA CGG GTT ACC CAG GAC CCT AAG CTC CAG ATG GGC AAG AAG CTC CCG CTC CAC CTC +260                                      CHO
thr leu pro gln ala leu pro gln tyr ala gly ser gly asn leu thr leu ala leu glu
ACC CTG CCC CAG GCC TTG CCT CAG TAT GCT GGC TCT GGA AAC CTC ACC GCC CTT GAA +280
ala lys thr gly lys leu his gln glu val asn leu val val met arg ala thr gln leu
GCG AAA ACA GGA AAG TTG CAT CAG GAA GTG AAC CTG GTG GTG ATG AGA GCA ACT CAG CTC
```

FIG.6(cont'd-c)

```
     CHO
+300 ───────────────
     gln lys asn leu thr cys glu val trp gly pro thr ser pro lys leu met leu ser leu
     CAG AAA AAT TTG ACC TGT GAG GTG TGG GGA CCC ACC TCC CCT AAG CTG ATG CTG AGC TTG +320                                                             +330
     lys leu glu asn lys glu ala lys val ser lys arg glu lys ala val trp val leu asn
     AAA CTG GAG AAC AAG GAG GCA AAG GTC AGT AAG CGG GAG AAG GCC GTG TGG GTG CTG AAC

*
+340 ───────────────                                              +350
     pro glu ala gly met trp gln cys leu leu ser asp ser ser gly gln val leu leu glu ser
     CCT GAG GCG GGG ATG TGG CAG TGT CTG CTG AGT GAC TCG AGT GGA CAG GTC CTG CTG GAA TCC +360                                                             +370
     asn ile lys val leu pro thr trp ser pro val gln pro met ala leu ile val leu
     AAC ATC AAG GTT CTG CCC ACA TGG TCC ACC CCG GTG CAG CCA ATG GCC CTG ATT GTG CTG
                                                                                    ▼
                                                     TM
+380 ──────────────────────────────────────────────────           +390
     gly gly val ala gly leu leu leu phe ile gly leu gly ile phe cys val arg cys
     GGG GGC GTC GGC GGC CTC CTG CTC TTC ATT GGG CTA GGC ATC TTC TGT GTC AGG TGC
                                                                   ▲
                                                                   CYT
+400                                                             +410 ────────────
     arg his arg arg gln ala glu arg met ser gln ile lys arg leu leu ser glu lys
     CGG CAC CGA AGG CAA GCA GAG CGG ATG TCT CAG ATC AAG AGA CTC CTC AGT GAG AAG
     ─ ─ ─
```

FIG.6(cont'd-d)

+420
lys thr cys gln cys pro his arg phe gln lys thr cys ser pro ile ---
AAG ACC TGC CAG TGC CCT CAC CGG TTT CAG AAG ACA TGT AGC CCC ATT TGA GGCACCAGGCA
            +430
            ←——— CYT ———

GGCAGATCCACTTCCAGCTCCCAGGTGTCTGCCCGTGTTCTCTGGTTAGCGCCCCCTCACTGTTGAGTG

TTCCTCTCTAGTTCCAGAGCTTAATCACACCCTCCTGCCCTGTTCCTGCCGGACCAGATGAATGTAGCAGATCCCACC

CTCTGCGGCCTCCTGTGTCCTCCTACACCCCATTCCCATCCAGCCCTTTCCTTCAAGCCTAGCCCTCTCTCATT

ATTTCTCTGACCCTCCCCACTGCTCATTTGGATCC

CONTRACEPTIVE DEVICE

1.0 INTRODUCTION

This invention relates to birth control or contraceptive devices. More particularly, this invention relates to contraceptive devices for males and females which provide novel immunological means for preventing the spread of sexually transmitted diseases. Contraceptive devices such as condoms and diaphrams, which typically only provide a physical barrier from the transmission of sperm and possibly disease causing agents have, by this invention, been provided with an additional immunological barrier which immunologically binds to a venereal disease causing agent, such as a bacteria or virus, present in a bodily fluid thereby neutralizing it and preventing the spread of the disease causing agent whose mode of introduction and infection typically is accomplished via sexual transmission of bodily fluids.

2.0 BACKGROUND OF THE INVENTION

2.1 CONTRACEPTIVES

The primary purpose of most contraceptive products is the prevention of pregnancy. This goal has been accomplished by a variety of means such as providing a physical barrier to prevent contact between sperm cells and ova [i.e. with condoms, cervical caps or contraceptive "sponges" (described in U.S. Pat. No. 4,393,871 which is hereby incorporated by reference]; altering the estrogen levels of the female with oral contraceptives so as to prevent the female from conceiving; and surgical sterilization procedures.

One of the most readily utilized contraceptives are condoms (otherwise equivalently referred to herein as prophylactics). Condoms have been known for decades to be reasonably effective in preventing conception so long as the condom maintains its physical integrity and, thereby, provide the physical barrier which keeps sperm within the condom sheath. Condoms also are known to provide a physical barrier to certain disease causing agents which might otherwise be passed along from one partner to the other during intercourse. To date, no other contraceptive device, composition or method is believed to provide the same degree of protection by physical barrier against transmission of infectious agents during intercourse as do condoms.

In principal, condoms have changed very little over the years. New materials and configurations have been utilized so as to improve characteristics as to strength, form (relating to their use as a male prostesis), the incorporation of spermicides for additional contraceptive activity and, in some cases, the addition of anti-bacterial or anti-viral effect.

U.S. Pat. No. 4,415,548 describes a spermicidally lubricated prophylactic and method for making the same wherein the lubricant causes the migration of the spermicide throughout the rolled prophylactic. It is asserted that this configuration enables manufacture and rolling of the prophylactic prior to the application of the spermicide.

U.S. Pat. Nos. 4,446,860 and 4,332,243 each discloses male and female (diaphram or cervical cap) prophylactics which includes a rupturable reservoir containing a medication which is released by mechanical pressure on the resevoir. The medication comprises antibiotics, antibacterials such as trichomonacides, moniliacides and, additionally, contraceptive (spermicide) compositions.

U.S. Pat. No. 4,232,675 discloses a prophylactic which includes a spermicidal ring structure on the prophylactic. This ring is stated to include a spearmicide such as ricinoleic acid, p-diisobutylphenoxpolyethoxyethanol and boric acid.

To date, however, the art has not disclosed any means other than the use of pharmacological agents in combination with a male or female barrier contraceptive or other prophylactic device for control of sexually transmissible disease causing agents.

2.2 MONOCLONAL ANTIBODIES

Monoclonal antibodies originated in 1979 when it was discovered that the fusion of a spleen lymphocyte (an antibody forming cell) with a myeloma or malignant cell would create a hybrid cell which had inherited characteristics of the both parent cells. [G. Kohler and C. Milstein, Nature 256:495–497 (1975); Eur. J. Immunol.6:511–519 (1976)] This hybrid cell was potentially immortal, as was the meyloma cell, and was capable of producing a single type of antibody specific to a particular antigen, as was the lymphocyte cell. The hybrid cell, which became known as a hybridoma, by virtue of its meyloma heritage, also was capable of being grown in culture to form a cell line, all cells of which generated the same antibody or immunoglobulin as the parental hybrid cell.

These two features offered a distinct advantage over conventional anti-sera. Anti-sera derived from vaccinated animals contain variable mixtures of polyclonal antibodies which never can be reproduced identically. However, monoclonal antibodies are highly specific immunoglobulins of a single type. The single type of antibody secreted by the hybridoma is specific to one antigenic determinant, or epitope, on the antigen, a very complex molecule having multiple antigenic determinants. Therefore, monoclonal antibodies raised against a single antigen may be distinct from one another depending on the determinant which induced their formation. However, for any particular hybridoma clone, all of the antibodies which it produces will be identical.

To date, monoclonal antibodies have been generated to a wide number of antigens and have demonstrated a wide range of utilities related to diagnostic analysis (i.e. radioimmuno assays), purification technology (i.e. antibody affinity chromatography), therapeutic treatments, vaccine production and even body imaging applications. For instance, U.S. Pat. No. 4,645,738 discloses the use of monoclonal antibodies in the diagnosis of T cell leukemias. U.S. Pat. No. 4,578,335 details the use of monoclonal antibodies in the purification of interlukin-2 receptors to homogeniety. U.S. Pat. No. 4,443,549 describes the production of monoclonal antibodies against surface antigens of bacteria which act as adhesins. A large variety of monoclonal antibodies specific to bacterial and viral epitopes also are available commercially. However, to date monoclonal antibodies have found application to sexually transmissible diseases in the diagnostic area. Monoclonal antibodies to many STD causitive agents are commercially available as from CLONATEC (departement BIOSOFT, 60, rue de Wattignies, 75580 Paris Cedex 12). The production of monoclonal antibodies to an immunosuppresive factor from the Human Immunodeficiency Virus (hereinafter equivalently referred to as HIV) or HIV infected cells is described in PCT Application number PCT/DK87/00035 which was published on Oct. 8, 1987 and is entitled, "Immunosuppressive Factor from Human Immunodeficiency Virus (HIV) or HIV Infected Cells or Cell Lines, Its Use, Corresponding Antibodies and Their Use".

2.3 SEXUALLY TRANSMITTED DISEASES

Sexually transmitted diseases (otherwise equivalently referred to herein as "STD" or "venereal diseases") represent some of the most common communicable diseases in the world today. In the last 20 years STD have been increasing in incidence. It has been estimated that on an annual basis, over 250 million people are infected worldwide with gonorrhea, for syphilis, over 50 million. Additionally, it is already believed that over 5 million have been infected by the virus or viruses (HIV viruses) which cause AIDS and, of which, the majority are believed to have been exposed through sexual contact.

The agents which are known to cause STD are varied but generally known to include viruses, bacteria, mycoplasma, protozoa, clamydia, ameoba and fungus. More specifically, they are known to include the following disease causing agents: *Chlamydia trachomatis, Neisseria gonorrhoeae, Treponema pallidum, Haemophilus ducreyi, Calymmatobacterium granulomatis,* Group B Streptococci, *Gardnerella vaginalis,* Shigella, Campylobacter, Salmonella, Human retrovirus such as the HIV viruses (HIV-1 and HIV-2), Herpes virus-1, Herpes virus-2, Hepatitis A, Hepatitis B, Cytomegalovirus and Papillomavirus.

The epidemiology, symptoms, diagnosis and treatment also varies for each of these STD causative agents. Special problems often encountered in dealing with these disease range from, for instance, perceived social stigmas and ease of transmission, to antibiotic resistant STD causative agents. The medical problems derived from STD range from physical discomfort to senility and death. The present AIDS epidemic is illustrative of an STD which, at present, has no cure.

In light of the seriousness of STD and the risk to public health, it has been a goal of the medical community to provide not only treatment for these diseases, but preventive measures as well. Indeed, it has been reported that the use of condoms not only provides a contraceptive effect but also, under appropriate circumstances, helps to prevent the spread of STD causative agents such as the AIDS virus. It has further been reported that the spermicide known as nonoxynol 9, an ingredient today in many contraceptive products, may have the effect of reducing the possibility of infection by HIV.

It is, therefore, an object of the present invention to provide novel and additional safeguards against the transmission of STD causative agents in the form of an acceptable contraceptive vehicle. It is also an object of this invention to provide related methods to prevent the spread of an STD causitive agent or agents.

3.0 SUMMARY OF THE INVENTION

Generally stated, this invention comprises a contraceptive device, such as a condom, cervical cap or contraceptive sponge, in association with a ligand to an STD causing agent. The ligand would be selected from either an antibody or a glycoprotein, such as CD4, which has an affinity for the STD causative agent and, preferably can neutralize that STD causitive agent. The combination of the contraceptive device with the associated ligand ,thereby, provides two barriers to the transmission of an STD causative agent: the physical barrier provided by the device itself and, significantly, an immunological barrier via the binding of the STD causative agent to the ligand (antibody or binding protein) associated with the device. More specifically, the ligand is attached or bound (i.e. covalently bound) to at least one surface (or in the case of the sponge, the surface and/or intersticial polymeric matrix) of the contraceptive device or is formed in conjunction (i.e. concurrently) with the device or is otherwise bound to an intermediate composition, such as a linker composition or fluid absorbing composition, which is in turn associated with or has been or is bound to the contraceptive device. The antibody or antibodies or binding protein may also be in association with other compositions such as detergents, enzymes, spermicides or anti-viral, antibacterial or other anti-STD modalities. The STD causative agent, once bound immunologically to the antibody, is also thereby bound to the contraceptive device and, thus, prevented from further infecting a receptive host.

It also is an aspect of this invention that the antibody or antibodies attached to the contraceptive may be characterized as either polyclonal or monoclonal antibodies having an affinity for the STD causative agent. The preferred binding protein, CD4, is a glycoprotein first identified as a component of the cell surface receptor for the HIV virus (HIV-1 or HIV-2). This protein is believed to act as an HIV receptor (i.e. initial binding site for infection of the cell by HIV) via recognition of the outer HIV envelope protein gp120. This protein has been reported to have a high degree of affinity for the gp120 protein.

This invention also provides for a method of preventing the spread of STD which comprises using the contraceptive device in association with an antibody to a STD disease causing agent during any activity which might risk infection by such an agent.

4.0 BRIEF DESCRIPTION OF THE FIGURES

FIG. 1-A shows a cross-sectional view of a condom coated on its interior surface with antibodies (γ) to an STD causitive agent;

FIG. 1-B shows a cross-sectional view of the antibody coated condom immediately after exposure to semen containing an STD causative agent (•);

5.0 DESCRIPTION OF THE INVENTION

5.1 IMMUNOLOGICAL BARRIER CONTRACEPTIVES AND THEIR PREPARATION

Broadly stated, this invention comprises a prophylatic type of contraceptive, such as a condom for males or a cervical cap or contraceptive sponge for females, which is provided in association with a ligand such as an antibody or antibodies or binding protein such as CD4 which have been generated against and/or have an affinity for a sexually transmissible disease causing agent.

The sexually transmitted disease causing agent which may be blocked or bound by the contraceptives of this invention generally include viruses and bacteria. More specifically, the virus may be an RNA or a DNA virus selected from the group consisting of Human retrovirus, Herpes virus-1, Herpes virus-2, hepatitis A, hepatitis B, Cytomegalovirus and papillomavirus. The STD disease causing bacteria may be *Neisseria gonorrhoeae, Treponema pallidum, Haemophilus ducreyi, Calymmatobacterium granulomatis,* Group B Streptococci, *Gardnerella vaginalis,* Shigella, Campylobacter and Salmonella. The STD disease causing agent blocked or bound by the contraceptives of this invention may also include mycoplasma, *Chlamydia trachomatis,* protoza, ameoba and fungus.

The term "ligand" as used herein broadly can be described as a selective adsorbant for a desired species, the ligate. Generally stated, in the practice of the invention herein, the ligand may be affixed, attached, bound, coupled to or otherwise placed in association with a solid-state contraceptive substrate, preferably the inner and/or outer surface of a condom, one or both sides or surfaces of a cervical cap or the surface and/or the intersticial spaces of a foamed polymeric contraceptive otherwise known as a contraceptive sponge.

Generally stated, in the practice of this invention the ligand would comprise an antibody or a binding protein, such as a glycoprotein (i.e. CD4), and the ligate would comprise a sexually transmissible disease causing agent. More specifically, the antibody or binding protein would have an affinity for or the capability of binding to, for instance, a protein or polysaccharide on the surface of the STD causitive agent. The ligands useful in the present invention may have varying degrees of selectivities depending on the precise nature and amount of the STD ligate to be adsorbed.

More specifically, antibodies useful with this invention have an affinity for a particular epitope on the sexually transmissible disease causing agent. The antibodies useful with this invention may be those known as monoclonal or polyclonal antibodies. It is central to the preferred embodiments of this invention that the ligand or ligands present provide the prophylatic with an immunological barrier, in addition to the physical barrier already provided by the membrane itself, to the passage of a disease causing agent from the prophylatic, which disease causing agent may be present in bodily fluids such as semen.

Figure 1A:
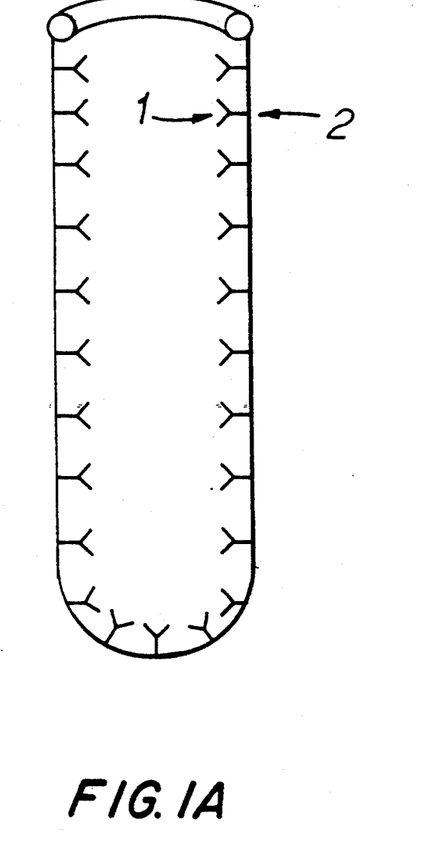
Figure 1B:
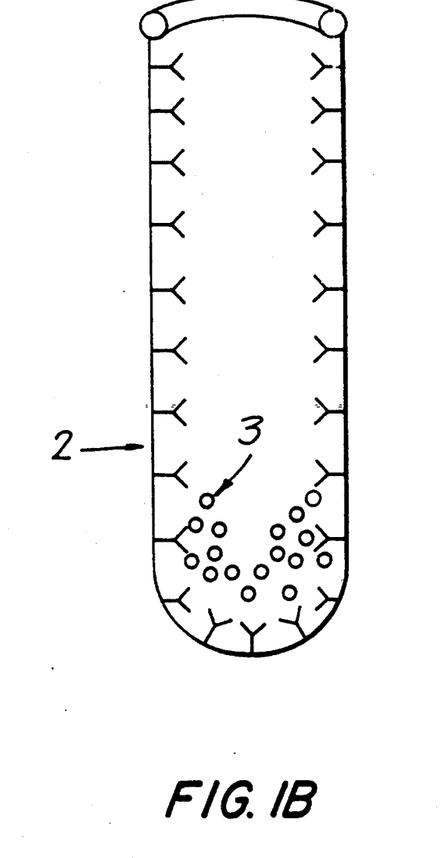
Figure 2:
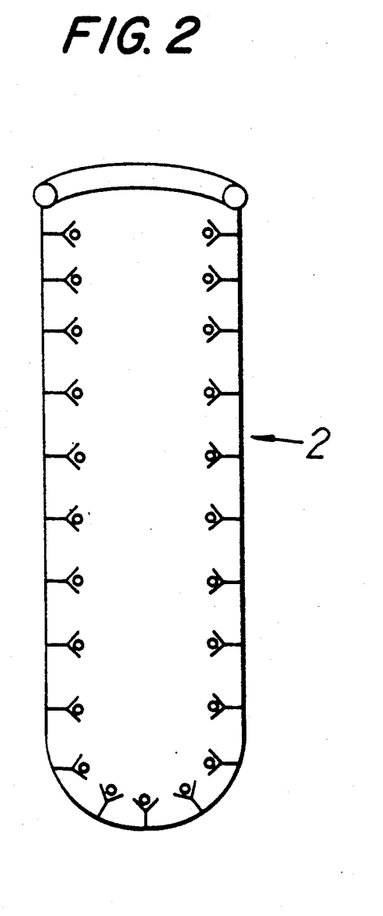
FIG. 2 shows a cross-sectional view of the condom of FIG. 1-A with the STD causitive agent (•) bound to the antibodies (γ) after a suitable period of time and after the STD causitive agent has been distributed throughout the interior of the condom by motion and the physical presence of the users genitalia.

The disease causing agents may be any of those commonly known to be sexually transmissible via bodily fluids and may include those set forth above such as bacteria, viruses, ameoba and others. Generally stated and as shown in FIGS. 1 and 2, the antibodies 1 or binding protein present in association with the prophylatic bind to the disease causing agent and, thereby, prevent its further movement outside of the prophylatic. An example of an antibody coated condom 2 is shown in FIG. 1-A. In FIG. 1-B a STD causitive agent 3 present in the semen is exposed to the interior surface 4 of the antibody coated condom. In FIG. 2 it can be seen that the STD causitive agent 3 has been bound to the antibodies 1 on the surface of the condom after a period of time and distribution of the semen within the condom.

In a preferred embodiment of this invention, the inside of a condom is coated with or has bound to (i.e. covalently attached) or otherwise attached thereto, with a ligand or ligands, preferably an antibody or binding protein to a disease causing agent or agents such as a virus or bacteria. The ligand which is present would act to immunologically bind to the disease causing agent against which it has been generated or has affinity, which agent may be present in bodily fluid such as semen. An antibody which immobilizes the disease causing agent or antigen, may also be referred to as a neutralizing antibody. For instance, if the neutralizing antibody is generated against and has an affinity for an epitope on the surface of HIV (such as to gp120, a glycoprotein present on the surface of HIV strains HIV-I or HIV-2) than virus present in a bodily fluid such as semen would bind immunologically with the antibody and, thereby, be immobilized and prevented from freely escaping the confines of a condom in spite of possible condom rupture. In this fashion, the spread of a disease causing agent would be blocked immunologically. The term 'neutralization' when referring to a virus means that the antibody, by combining with the virus, acts to prevent attachment of the virus to the host cell membranes, thereby preventing virus entry into the cell. Since viruses are intracellular parasites and can only live in the host cells, the antibody kills the virus indirectly by cutting off its access to possible host cells.

Figure 4:
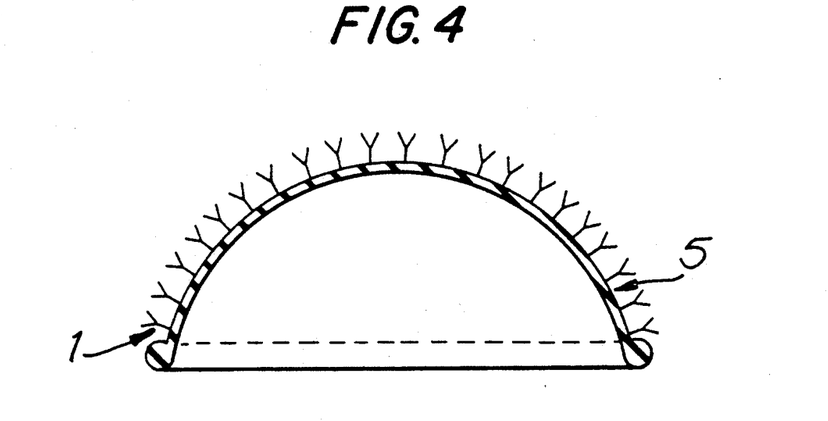
FIG. 4 shows a cross-sectional view of a cervical cap having antibodies (γ) to an STD causitive agent attached to one side of its surface membrane.

In another preferred embodiment, the ligand, preferably an antibody 1 to an STD causitive agent, is coated onto one or both sides of a cervical cap 5 (otherwise commonly known as a diaphram) as shown in FIG. 4. In the same manner as described above with the condom, the antibodies associated with the diaphram would serve to bind any disease causing agent present in bodily fluids received from a sexual partner.

Once the diaphram is removed the antibody-antigen (STD disease causing agent) bond can be broken by solutions known in the art (such as acetic acid) and the disease causing agent can thereby be rinsed from the diaphram. After rinsing, the diaphram may be used again, with the ligand (i.e. antibodies) providing a continued immunological barrier against later possible exposure to the STD disease causing agent.

Figure 5:
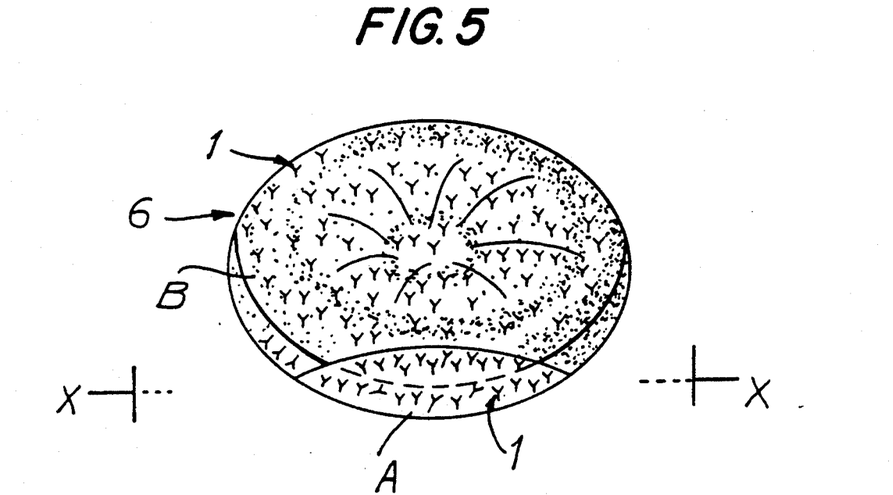
FIG. 5 shows a cross-sectional view of a contraceptive sponge having antibodies (γ) to an STD causitive agent associated with the exterior B of the sponge and integral to the interior A of the sponge structure.

In an additional preferred embodiment, the ligand, preferably antibodies 1 or binding protein to an STD causitive agent, may be associated with, bound to or otherwise attached to the surface and/or impregnate the intersticial matrix of the foamed polymeric material of a contraceptive commonly known as the contraceptive 'sponge' 6 (such as that described in U.S. Pat. No. 4,393,871 hereby incorporated by reference) as shown in FIG. 5. The foamed polymeric material is preferably formed from a urethane polymer. In this embodiment, the disease causing agents in the bodily fluids would, upon contact, immunologically bind to the antibodies 1 or binding protein present in the interior A (as shown on the partial cross-sectional view X) and/or on the surface B of the sponge. After use, this contraceptive may be disposed of by the user.

Figure 3:
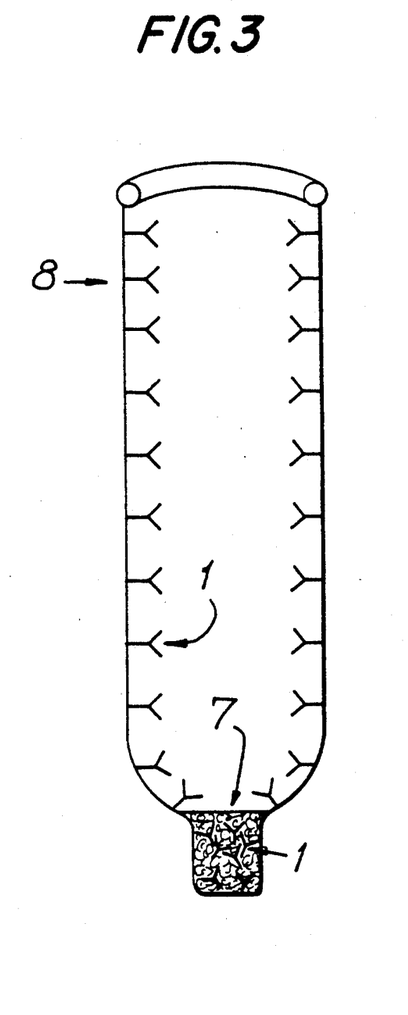
FIG. 3 shows a cross-sectional view of a prophylatic having a hydrophylilic fibrous, water-insoluble hydrogel incorporating antibodies (γ) to an STD causitive agent at the distal tip.

In a further preferred embodiment, a condom 8 is provided with an absorbant hydrophillic material 7, preferably at its closed or distal end. This material also may be otherwise distributed throughout the interior of the condom. This composition may be a fibrous material alone (i.e. paper derived) or in combination with particles of water-insolubile hydrogel, see FIG. 3, such as that commonly utilized in disposible diapers and as disclosed in U.S. Pat. No. 4,610,678. Water-insoluble hydrogels are polymeric materials which are capable of absorbing large quantities of water. Additionally, the absorbant material is preferably in association with a ligand such as antibodies 1 or a binding protein to an STD disease causing agent or agents. The absorbant material and/or hydrogel is preferably disposed at a reservoir at the distal tip of the condom and also may be separated from contact with the user by a wicking type of material or cloth. In this embodiment the disease causing agent or agents, upon being absorbed into the material and/or hydrogel with the bodily fluids would then be immunologically bound to the ligand present in association with the material and/or hydrogel matrix and, thereby, be prevented from escaping the interior of the condom.

In another embodiment of this invention it is preferred that the ligand is coupled to material such as a latex bead, a polyacrylamide gel bead or Sephadex bead (commercially available from Pharmacia Fine Chemicals; and which is made from a mixture of dextran and epichlorohydrin) and that these materials, once the ligand is attached, be provided (i.e. as a 'powder') to the contraceptive (i.e. the interior surface of a condom). It is optional to attach these ligand activated materials to the contraceptive device since their binding and neutralization of the STD causitive agent would occur whether they are attached or not attached to the contraceptive device.

Generally stated, the ligand when utilized with the particular contraceptive also may be in association with spermicides, such as nonoxynol-9, or lubricants commonly in use with contraceptives today. Furthermore, anti-bacterial compounds which are useful in a topical form (i.e. tetracycline); anti-viral compounds (i.e. Zidovudine) or proteolytic compounds (i.e. certain enzymes or proteases) or other commercially available bacterialcidal compounds (i.e. hexachlorophene) may be present in conjunction with the ligand to the STD causitive agent. A partial list of compounds which could be used in combination with the ligand-activated contraceptive of this invention are: Carrisyn (polymannoacetate; Carrington Laboratories); Doxorubicin hydrochloride (adriamycin; Adria Laboratories); Eflornithine (alpha-difluoro- methylornithine or DFMO; Merryl Dow); Ganciclovir (9-[(1,3-dihydroxy-2-propoxy) methyl]guaine or DHPG; Syntex); D-Penicillamine (3-mercapto-D-valine; Carter-Wallace); Peptid-T (Pennisula Laboratories); Ribavirin (1-beta-D-ribofuranosyl-1, 2,4-triazole-3-carboxamide; ICN Pharmaceuticals); Rifabutin (ansamycin LM427; Adria Laboratories); Zidovudine (3'-azido-3'-deoxythymidine or AZT; commercially available as Retrovir; Burroughs Wellcome).

The antibodies of this invention may be generated against a particular STD disease causing agent or may be selected from those already commercially available, such as those used for diagnostic or purification purposes. As noted above Monoclonal antibodies to many STD causitive agents are commercially available as from CLONATEC (departement BIOSOFT, 60, rue de Wattignies, 75580 Paris Cedex 12). Broadly stated, the antibody may be in association with or bound to the prophylatic material either ionically or covalently and may be in association with or bound to the prophylatic material directly or via an intermediate compound or material, such as latex particles or fibrous material, which intermediate material may be attached to the prophylatic. The antibodies may be attached to the prophylatic in the same manner as they are attached to solid state supports in other applications, such as in affinity chromatography columns, latex beads (i.e. for agglutination assays) or as with certain immunoaffinity membranes. It also is an embodiment of this invention where the prophylatic is formed with antibodies present during the molding process so that they are formed as an integral part of the prophylatic.

It also is within the scope of this invention that more than one kind or type of antibody to a specific STD disease causing agent or agents may be present in the prophylatic. For instance, two or more varieties of antibody may be present, each variety of which might have an affinity against a different epitope on the same STD disease causing agent or, alternatively, each variety might have an affinity against different STD disease causing agents (i.e. HIV and Herpes and/or gonococcus bateria), or any combination of the above. Use of a prophylatic of this embodiment would act to simultaneously prevent the spread of multiple STD disease causing agents which may be present in exchanged body fluids.

Figure 6:
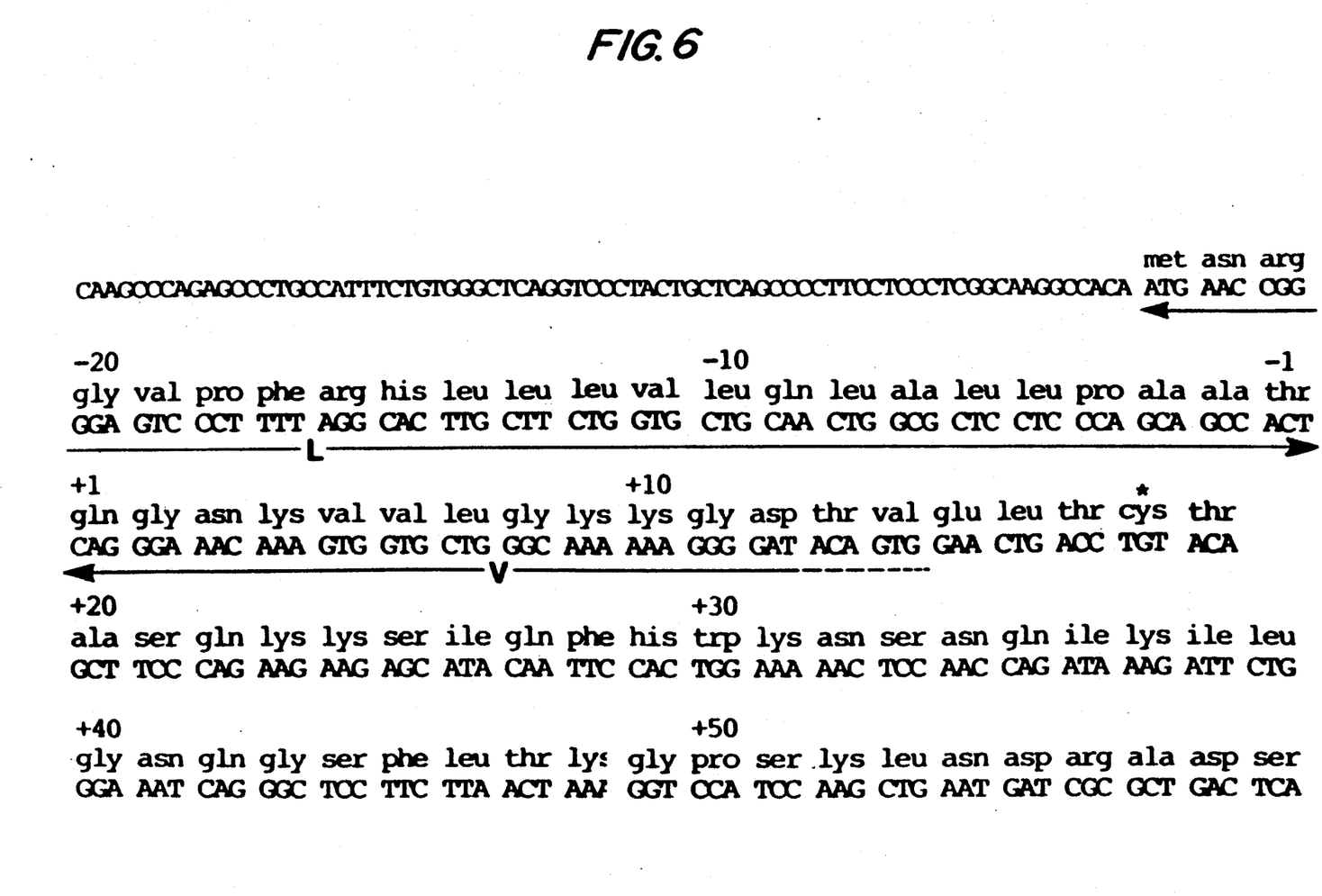
FIG. 6 shows the nucleotide and amino acid sequence of the glycoprotein CD4; numbers above amino acid sequence designate amino acid residue positions; numbers on right show nucleotide positions; extracellular cysteines marked with *;L represents leader sequence; ·V represents the variable or immunoglobulin-like region sequence; J represents the joining-like region sequence; TM represents the transmembrane region sequence; CYT represents the cytoplasmic region sequence-indicated by arrows below the sequence; Potential N-linked glycosylation sites also indicated by CHO.

The other preferred ligand for use in the practice of this invention is a binding protein known as CD4. Without wishing to be bound by any theory or mechanism, it is believed that this glycoprotein is present on the surface of T4 cells, which cells are preferentially infected by HIV. It is believed that HIV (particularly its surface glycoprotein gp120) directly interacts with and initially binds to the CD4 surface antigen during infection of a T4 cell. It has been reported that soluble CD4 neutralizes HIV infectivity in vitro [Smith, D. H. et al., Science, 238, 1704–1707 (1987)]. The amino acid sequence of CD4 and the nucleotide sequence coding for it are shown in FIG. 6. It is believed that amino acids +1 to about +374 are actually exposed on the surface of the T4 cell to interaction with HIV and, therefore, this portion (1–374) of the sequence would be particularly useful in the practice of this invention. This protein may be produced according to the procedure set forth in Maddon, P. J. et al, Cell, 42, 93–104 (1985) which is hereby incorporated by reference. Any mutation or fragment of the CD4 protein which would bind to gp120 is also within the scope of this invention. CD4 may also be produced via the procedure described in Lasky, L. A. et al, Cell, 50, 975–985 (1987) which is hereby incorporated by reference. In that procedure a human CD4 cDNA clone was isolated from a gamma gt10 cDNA library derived from the H9/HTLV-IIIs cell line (Muesing et al., Nature, 313, 450–458 (1985)), utilizing the sequence information presented by Maddon, P. J. et al, *Cell,* 42, 93-104 (1985). The complete CD4 cDNA sequence was expressed under the transcriptional control of an SV40 early promoter in CHO cell lines as a membrane-bound glycoprotein by utilizing a similar SV40-derived vector (Muesing, M. A. et al., *Cell,* 48, 691-701 (1987). Cell lines expressing high levels of CD4 were selected and analyzed by immunoprecipitation using OKT4 monoclonal antibodies [Dalgleish, A. et al., *Nature,* 312, 763-766 (1984); Klatzmann, D. et al., *Nature,* 312, 767-768 (1984); McDougal, J. et at., *J. Immunol.,* 135, 3151-3162 (1985); McDougal, J. et al., *Science,* 231, 382-385 (1986); McDougal, J. et al., *J. Immunol.,* 137, 2937-2944 (1986); Maddon, P. J. et al, *Cell.* 47, 333-348 (1986)]. Human CD4 may also be produced according to the procedure set forth in Hussey, R. E. et al., *Nature,* 331, 78-81 (1988) or Fisher, R. A. et al. *Nature* 331, 76-78 (1988) which are hereby incorporated by reference.

The HIV envelope glycoprotein known as gp120 is also believed to be involved in the recognition, binding and infection process of T4 cells by HIV. Therefore, it is also within the scope of this invention that antibodies to gp120 may also be utilized to bind HIV present in bodily fluids onto the contraceptives set forth and described herein. The procedure for producing antibodies to gp120 is set forth below in section 5.2.

Contraceptive prophylatics, such as condoms, are typically manufactured by dipping a rod or phalic shaped metal or ceramic form into a natural rubber latex, usually warm, bath.

The latex coats the form which has been inserted to a predetermined depth. The form is removed from the latex bath after a certain desired period of time and the latex is material is allowed to dry. The latex, once dry, is typically removed from the form by rolling it off of the end which coinsided with the surface of the latex bath during the dipping stage. It is after this stage that spermicides are typically applied to the condom (See U.S. Pat. No. 4,415,548 which is hereby incorporated by reference).

In the practice of this invention, however, it is preferred that the condom form or mold be exposed to or dipped or otherwise coated with the ligand, such as an antibody to the STD causative agent or a protein such as CD4, prior to dipping the form into the latex bath. In this fashion the condom is formed on the form or mold with the antibodies entrapped and exposed on the inner surface of the condom. It also is preferred that the ligand may be provided to the interior of the condom in an alternate fashion, such as through a tube communicating with the interior of the condom or the end of the molding form or through multiple holes radiating out from a hollow molding form so that the ligand may be applied or bound to the condom surface at any time during or after the formation of the condom. It is also within the scope of this invention that the ligand is applied to the interior of the condom after it has been removed from the form. In another embodiment the ligand may be present in the latex bath so that the condom may also be formed with the active ligand present in the latex matrix. It is preferred the temperature and other ingredients present in the latex bath would not inactivate or denature the ligand, thereby preserving its neutralization characteristics.

A wide variety of techniques to attach antibodies to a polymeric surface such as a membrane, natural or synthetic, are available and known to those skilled in the art and any of those techniques are applicable with this invention so long as the antibody retains its activity after attachment and the means of attachment does not compromise the integrity of the condom membrane.

Biologically active proteins such as antibodies, antigens, glycoproteins and enzymes can be attached to insoluble solid supports comprising latex spheres carrying lateral chains terminating in primary amine functions, by reaction of active groups of the amino acids of the protein chain with the primary amine groups of the support. In Molday, R. S. et al., *The Journal of Cell Biology,* Vol. 64, 75-88 (1975) and Lim, R. W. et al., *Biochimica et Biophysica Acta,* Vol. 394, 377-387 (1975) the fixation of antibodies on latex spheres is described by coupling the antibodies through the intermediary of their primary amine functions via covalent bonds onto the latex spheres, which themselves have been previously provided with lateral chains terminating by a primary amine function activated by the action of activators such as glutaraldehyde, cyanogen bromide or water soluble carbodiimide. Similarly, a latex contraceptive such as a condom could be treated or activated during or after formation (molding) after which a sufficient amount (typically a saturation or excess amount) of the ligand would be provided to coat and be coupled to the interior activated latex surface of the contraceptive. The interior surface of the condom has a known area to which the appropriate amount of ligand need to effectively coat all or part of the surface can easily be determined using methods known in the art to bind ligands to other solid state supports.

U.S. Pat. Nos. 4,419,444 and 4,217,338, which are both hereby incorporated by reference, also teach methods for chemically binding organic compounds containing carbohydrate residues, i.e. antibodies and glycoproteins, onto a support, i.e. latex, bearing at least one reactive —NH2, in which at least one —CH2OH group of the carbohydrate residue is transformed into a —CHO group, by oxidation and then the —CHO groups thus obtained are reacted with at least a reactive —NH2 carried by the side chains covalently bound on a solid, insoluble support. The side chains are chosen from among amines, polyamines, diacids, aminoacids, hydrizines and are eventually coupled, by the intermediary of their reactive —NH2, with a nitrogen containing compound chosen from aliphatic or aromatic amines, aliphatic or aromatic hydrizines, or amino acids, comprising eventually jointly a —SH group and a —NH2 group. In that process the condensation and coupling agents may be selected from the groups consisting of glutaraldehyde, N-hydroxyl-succinimide and a totally or partially water-soluble carbodiimide of the general formula R—N=C=N—R in which R represents an alkyl radical having 2 to 12 carbon atoms; a cycloalkyl radical having 5 or 6 carbon atoms; a mono-aryl substituted lower alkyl radical; a mono-aryl radical; a lower alkyl radical substituted by a morpholinyl group; a lower alkyl radical radical substituted by a piperidyl group; an ethylpiperidyl group; a lower dialkylamino radical; a lower alkyl radical substituted by a pyridyle group, their acid addition salts with acids and their quaternary ammonium salts, the two R radicals being identical or different. Similarly, a latex contraceptive such as a condom could be treated or activated during or after formation (molding) after which the ligand would be provided and coupled to the activated latex surface of the contraceptive.

In addition, the manner of attaching antibodies to latex beads for latex agglutination assay (U.S. Pat. No.

4,181,636 herein incorporated by reference) or by adsorbtion onto the condom surface or covalently bonding the antibody or glycoprotein to the surface of the condom [a water insoluble polymer as in U.S. Pat. No. 3,645,852 herein incorporated by reference (using cyanogen halide)], would be useful in the practice of this invention for attaching or immobilizing antibodies or glycoproteins onto the condom membrane. Several methods of attaching enzymes onto solid phase supports are reviewed in Goldman et al., Biochemical Aspects of Reactions on Solid Supports, Academic Press, New York, 1971. Antibodies also have been linked to beads of Sepharose 4B (Pharmacia Fine Chemicals) for purposes of affinity chromatography. Antibodies also have been bound to cross linked acrylic polymer beads U.S. Pat. No. 3,957,741).

It also is within the scope of this invention that the ligand, such as an antibody to an STD causitive agent or the protein CD4, is attached to any other acceptable natural membrane or synthetic polymeric membrane such as an immunoaffinity membrane (i.e. such as the commercially available "Immunodyne" membrane, Pall BioSupport, Glen Cove, N.Y.) which is in turn utilized soley as the prophylactic or is alternatively placed in contact with the interior surface of a condom formed from another material in such a fashion that the ligand bound or attached to the inner membrane of the bi-membrane structure would be exposed to the semen of the user.

In another preferred embodiment, the ligand, such as an antibody to an STD causitive agent or CD4, is attached to a hydrophillic fiberous material and water-insoluble hydrogels (U.S. Pat. No. 4,610,678 incorporated herein by reference) in association with the inner surface of condom, with said antibody being mixed with or otherwise in association with said material. It is preferrable in the practice of this invention that this material be predominantly located at the tip or in a reservoir at the tip (closed end) of the condom and thereby be in a position to absorb any bodily fluids such as semen.

5.2 PREPARATION OF ANTIBODIES

The antibodies useful in the present invention may be generated by immunizing a mouse or other suitable host with a desired antigen which, in the practice of this invention, would comprise an STD causative agent or any portion of that agent which would act to stimulate an immune response in the immunized animal and thereby generate antibodies against the STD causative agent These antibodies may be isolated from the antisera of the immunized host by methods known to those of skill in the art. The antibodies may then be characterized for their affinity against the STD causative agent. The preferred antibody for use in this invention would comprise one which has the capability to selectively form an immunological bond with the STD causative agent or otherwise complex with this agent (as also equivalently used herein the antibodies may be referred to as "neutralizing antibodies").

The antibodies of this invention preferably would comprise monoclonal antibodies obtained essentially utilizing the process described by Milstein and Kohler and reported in *Nature*, 256:495-497, 1975. The antigen used to immunize the mouse or other appropriate host would comprise an STD causative agent, such as those listed below in this section, or any form or portion of that agent (i.e. killed or fragmented) which would act to stimulate an immune response in the immunized animal and thereby generating antibodies against the STD causative agent. Pure or dilute cultures or serum or other bodily fluids containing an STD causative agent also may be used in the immunization procedure.

Somatic cells which have the capability of producing antibodies, i.e. B cells, are preferable for fusing with myeloma cells, preferably a B-cell myeloma line. Lymph nodes and spleens of the immunized animals are the preferred sources. Mouse and rat lymphocytes also are preferred because of the greater probability of stabile fusions with mouse or rat originated myeloma cell lines. It is within the scope of this invention, however, that other animal or human sources may be used as the antibody producing cell.

A wide variety of myeloma cell lines known to those of skill in the art may be used in the hybridoma fusion procedure. Typically, these cell lines have selective deficiencies which enable screening and selection of hybridoma cells generated after the fusion from those other cells which have not fused to form hybridomas. Many of these cell lines have been described in the literature, for instance, P3/NSI/1-Ag-4-1 and P3/X63-Ag 8 were described in Kohler and Milstein [Eur. J. Immuno. 6: 511519 (1976)] and Sp2/O -Ag14 was generated by Shulman et al [Nature 276: 269-270 (1978)].

Hybridomas are generated by fusion of the antibody producing cells under conditions favorable to hybridization occurring, i.e. mixing somatic cells with the myeloma cells at about a 10:1 proportion in a medium which promotes the fusion. A typical fusion promoting medium is polyethelene glycol (PEG) although others, such a viral agents and electrical fields, may also be used. Hybridomas are selected from unfused cells preferably by culturing the cells after the fusion procedure in a medium which would support the existance of a fused cell but not that of an unfused cell. The cells are typically selected against hypoxanthine/aminopterin/-thymidine (HAT) medium, a medium in which the fused cells survive due to the fact that they are positive for the presence of hypoxanthine phosphoribosyl transferase (HPRT) whereas the myeloma cells used lacked HPRT. Standard assay methods such as enzyme linked immunoassays and radioimmunoassays may be used to determine whether any hybridomas selected by this technique produce antibodies. Typically, less than 30% of the hybridomas generated produce antibodies.

Hybridoma cell lines may be propogated and obtained in several ways. In one way the cell line is injected into an acceptable animal host which was of the type used as the source of the myeloma and somatic cells for the fusion. The injected animal procedes to develop tumors (from the myeloma trait of the hybridoma) which secrete antibody. The antibodies thus generated may be tapped by draining off the serum or ascites fluid of the animal. This method provides monoclonal antibodies in a very high concentration. Another method involves the in vitro culturing of the hybridomas in a suitable culture vessel, and isolating the monoclonal antibodies from the culture medium. Finally, many varieties of monoclonal antibodies are available commercially. A monoclonal antibody which would effectively bind to an STD causative agent would be appropriate for use with this invention in combination with the contraceptive device. For instance, a monoclonal antibody to HIV surface glycoprotein gp120 which would be useful in the contraceptives of this invention have been produced as follows and as described in Lasky, L. A. et al., *Cell*, 50, 975-985

(1987): Mice were immunized with 30 ug of purified gp120 seven times over a period of seven months. Spleens from the immunized mice were disrupted and fused with NP3×63-Ag8.653 myeloma cells and were selected in HAT medium. Individual wells were analyzed for reactivity with purified gp120 by an ELISA assay. Cells in positive wells were cloned, and the monoclonal antibodies produced by each hybridoma were analyzed in the I125 gp120-CD4 blocking assay described in Lasky, L. A. et al.,supra. The assay was initially characterized by adding increasing quantities of either the OKT4 or OKT4a CD4 monoclonal antibodies to the binding assay [Dalgleish, A. et al., *Nature*, 312, 763–766 (1984); Klatzmann, D. et al., *Nature*, 312, 767–768 (1984); McDougal, J. et al., *J. Immunol.*, 135, 3151–3162 (1985); McDougal, J. et al., *Science*, 231, 382–385 (1986); McDougal, J. et al., *J. Immunol.*, 137, 2937–2944 (1986); Maddon, P. J. et al, *Cell*, 47, 333–348 (1986)]. This gave the expected inhibition of gp120 binding by OKT4a, and lack of inhibition by OKT4. All of the murine gp120 monoclonal antibodies were tested in this assay, and two, termed 5C2E5 ans 7F11, were found to block the gp120-CD4 interaction effectively. 5C2E5 Fab fragments were isolated after digestion with papain on an ion exchange column as described by Garvey, J. et al., Methods in Immunology: A Laboratory Text for Instruction and Research (Reading, Mass.: Benjamin-Cummings) (1977).

It is generally within the scope of this invention that the sexually transmitted disease causing agent which can be used as an antigen in the generation of a monoclonal antibody may be a virus or a bacteria. More specifically, the virus may be an RNA or a DNA virus selected from the group consisting of Human retrovirus (as noted above), Herpes virus-1, Herpes virus-2, hepatitis A, hepatitis B, Cytomegalovirus and papillomavirus. The STD disease causing agent used as an antigen in the generation of a monoclonal antibody may also consist of mycoplasma, *Chlamydia trachomatis*, protoza, ameoba and fungus. The STD disease causing bacteria used as an antigen in the generation of a monoclonal antibody may also be *Neisseria gonorrhoeae, Treponema pallidum, Haemophilus ducreyi, Calymmatobacterium granulomatis*, Group B Streptococci, *Gardnerella vaginalis*, Shigella, Campylobacter and Salmonella.

5.3 METHOD FOR PREVENTING THE TRANSMISSION OF AN STD CAUSITIVE AGENT

This invention also comprises a method for preventing the spread of an STD causitive agent between individuals. Generally stated, this method comprises: a) providing a contraceptive device comprising a physical and immunological barrier to sexually transmitted disease causing agents and b) using said contraceptive during coitus whereby the transmission of any sexually transmitted disease causing agents emitted by at least one of said individuals during coitus between said individuals will be blocked by said contraceptives physical and immunological barriers with said venereal disease causing agent being immunologically bound to said contraceptive device.

The preferred contraceptive device is one selected from the group consisting of a condom, a cervical cap and a foamed polymeric material (i.e. polyurethane). The immunological barrier is provided by a ligand to a sexually transmitted disease causing agent, broadly stated, which is in association with the contraceptive. The ligand may be one selected from the group consisting of an antibody (monoclonal or polyclonal; preferably a neutralizing antibody) and a glycoprotein (i.e. CD4). The ligand is preferably covalently attached to the contraceptive device.

It can, therefore, be concluded from the above disclosure that the contraceptive devices and method set forth herein can assist in the prevention of the spread of a wide variety of harmful STD causitive agents.

While the various contraceptive embodiments herein have been described in detail, it is obvious that this invention is not to be considered as limited to the exact forms disclosed, and that changes in detail and construction of the contraceptives may be made without departing from the spirit and scope of this invention.

I claim:

1. A contraceptive device comprising a condom in association with an antibody to a sexually transmitted disease causing agent wherein said antibody is chemically bound to the condom.

2. The contraceptive device of claim 1 wherein the antibody is covalently bound to the inner surface of the condom.

3. The contraceptive device of claim 1 wherein the antibody is bound to a second solid state support which is attached to said condom.

4. The contraceptive device of claim 3 wherein the second solid state support is selected from the group consisting of latex particles, Sephadex and polyacrylamide gel beads.

5. A contraceptive device comprising a condom in contact with a cell surface receptor for a sexually transmitted disease causing agent.

6. The contraceptive device of claim 5 wherein the cell surface receptor is CD4.

7. The contraceptive devices of claim 5 wherein the sexually transmitted disease causing agent is a virus.

8. The contraceptive device of claim 5 wherein the sexually transmitted disease causing agent is a bacteria.

9. The contraceptive device of claim 7 wherein the virus is selected from the group consisting of Human retrovirus, Herpes virus-1, Herpes virus-2, hepatitis A, hepatitis B, Cytomegalovirus and papillomavirus.

10. The contraceptive device of claim 5 wherein the sexually transmitted disease causing agent is selected from the group consisting of mycoplasma, *Chlamydia trachomatis*, protoza, ameoba and fungus.

11. The contraceptive device of claim 8 wherein the bacteria is selected from the group consisting of *Neisseria gonorrhoeae, Treponema pallidum, Haemophilus ducreyi, Calymmatobacterium granulomatis*, Group B Streptococci, *Gardnerella vaginalis*, Shigella, Campylobacter and Salmonella.

12. The contraceptive device of claim 5 wherein the cell surface receptor is bound to the condom.

13. The contraceptive device of claim 12 wherein the cell surface receptor is covalently bound to the inner surface of the condom.

14. The contraceptive device of claim 12 wherein the cell surface receptor is bound to a second solid state support which is contacting said condom.

15. The contraceptive device of claim 14 wherein the second solid state support is selected from the group consisting of latex particles, Sephadex and polyacrylamide gel beads.

16. The contraceptive device of claim 5 wherein the condom is formed of material selected from the consisting of natural membrane, synthetic polymer and latex.

17. The contraceptive of claim 16 wherein the material is an immunity affinity membrane.

18. The contraceptive of claim 16 wherein the material is impermeable to the passage of bacterial and viral disease causing agents.

19. The contraceptive device of claim 5 further comprising a hydrophillic material in association with the inner surface of condom with said antibody being in association with said material.

20. The contraceptive device of claim 19 wherein said hydrophillic material absorbs bodily fluids.

21. The contraceptive device of claim 19 wherein said hydrophillic material is located predominantly at the proximal end of said condom.

22. The contraceptive device of claim 19 wherein said hydrophillic material comprises a mixture of hydrophillic fibers and particles of water-insoluble hydrogels.

23. The contraceptive device of claim 5 further comprising an anti-viral composition.

24. The contraceptive device of claim 5 further comprising one selected from the group consisting of an anti-bacterial composition and bateriacidal compositions.

25. The contraceptive device of claim 5 further comprising a proteolytic agent.

26. The contraceptive device of claim 25 wherein the proteolytic agent is selected from the group consisting of enzymes and detergents.

27. The contraceptive device of claim 1 further comprising at least a second antibody to said sexually transmitted disease causing agent.

28. The contraceptive device of claim 27 further comprising at least a second antibody to at least a second sexually transmitted disease causing agent.

* * * * *